(12) United States Patent
Ansley

(10) Patent No.: US 9,550,009 B1
(45) Date of Patent: Jan. 24, 2017

(54) AIR TREATMENT SYSTEMS AND METHODS

(71) Applicant: Prolitec Inc., Milwaukee, WI (US)

(72) Inventor: Matthew Ansley, Muskego, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 14/930,345

(22) Filed: Nov. 2, 2015

Related U.S. Application Data

(60) Provisional application No. 62/220,155, filed on Sep. 17, 2015.

(51) Int. Cl.
*A61L 9/14* (2006.01)
*B65D 83/60* (2006.01)

(52) U.S. Cl.
CPC ......... *A61L 9/14* (2013.01); *B65D 83/60* (2013.01)

(58) Field of Classification Search
CPC .................................... A61L 2/10; A61L 9/14
USPC .......................................................... 422/24
See application file for complete search history.

(56) References Cited

U.S. PATENT DOCUMENTS

| | | | | |
|---|---|---|---|---|
| 2,607,573 | A | * 8/1952 | Hession, Jr. | ........... A61L 9/14 239/214.21 |
| 7,377,493 | B2 | * 5/2008 | Thomas | .............. A61L 9/12 261/121.1 |
| 7,712,683 | B2 | 5/2010 | Robert et al. | |
| 7,930,068 | B2 | 4/2011 | Robert et al. | |
| 8,855,827 | B2 | 10/2014 | Weening et al. | |
| 2003/0192922 | A1 | * 10/2003 | Ceppaluni | ............ A61L 9/14 222/642 |
| 2006/0210421 | A1 | * 9/2006 | Hammond | ............ A61L 9/03 422/3 |
| 2009/0236362 | A1 | * 9/2009 | Helf | .................. A01M 1/2038 222/52 |

* cited by examiner

*Primary Examiner* — Sean E Conley
(74) *Attorney, Agent, or Firm* — Seed IP Law Group LLP

(57) ABSTRACT

A system is provided for treating a space at least partially enclosed by a wall with an aerosolized compound. The system includes a discharge unit, a liquid diffusion appliance, and a conduit extending therebetween. The discharge unit is mounted to a first side of the wall and includes an aerosol outlet in fluid communication with the space to be treated. The liquid diffusion appliance is mounted to a second side of the wall and includes a control system for operating the liquid diffusion appliance to generate and discharge an aerosolized compound from an appliance outlet. The conduit couples the appliance outlet with the discharge unit and defines a passageway through the wall through which the aerosolized compound travels to be discharged into the space to be treated.

14 Claims, 3 Drawing Sheets

AIR TREATMENT SYSTEMS AND METHODS

BACKGROUND

Technical Field

The present disclosure relates generally to air treatment systems and methods and, more specifically, to air treatment systems and methods for treating a space at least partially enclosed by a wall with an aerosolized compound generated by a liquid diffusion appliance that is located remote from the space to be treated.

Description of the Related Art

Liquid diffusion appliances are known which have the ability to dispense scent or other aerosolized matter throughout the atmosphere of a desired space but may suffer from various drawbacks, including, for example, the unsightly presence of the liquid diffusion appliance in the space to be treated and/or the presence of the liquid diffusion appliance in a space that is accessible to the general public, which may subject the liquid diffusion appliance to tampering or damage.

BRIEF SUMMARY

The air treatment systems and methods described herein enable treating a space at least partially enclosed by a wall with an aerosolized compound generated by a liquid diffusion appliance that is located remote from the space to be treated, including, in particular, on an opposing side of the wall.

At least one embodiment of a system for treating a space at least partially enclosed by a wall with an aerosolized compound may be summarized as including: a discharge unit mounted to a first side of the wall, the discharge unit having an aerosol outlet in fluid communication with the space to be treated; a liquid diffusion appliance mounted to a second side of the wall opposite the first side of the wall, the liquid diffusion appliance including the compound in liquid form to be aerosolized and including a control system for operating the liquid diffusion appliance to generate the aerosolized compound from the liquid compound and to discharge the aerosolized compound from an appliance outlet of the liquid diffusion appliance; and a conduit coupling the appliance outlet of the liquid diffusion appliance with the aerosol outlet of the discharge unit, the conduit defining a passageway through the wall through which the aerosolized compound travels to be discharged into the space to be treated.

At least one embodiment of an installation method may be summarized as including: mounting a discharge unit to a first side of a wall, the discharge unit having an aerosol outlet that is in fluid communication with a space to be treated; mounting a liquid diffusion appliance to a second side of the wall opposite the first side of the wall, the liquid diffusion appliance including a compound in liquid form to be aerosolized and including a control system for operating the liquid diffusion appliance to generate an aerosolized compound from the liquid compound and to discharge the aerosolized compound from an appliance outlet of the liquid diffusion appliance; and coupling the appliance outlet of the liquid diffusion appliance to the aerosol outlet of the discharge unit via a conduit extending into a cavity of the wall.

At least one embodiment of a kit for positioning a liquid diffusion appliance remote from a space to be treated by an aerosolized compound discharged by the liquid diffusion appliance may be summarized as including: a wall mountable discharge unit comprising a main body, the main body including a mounting flange, a stem projecting from one side of the main body which includes an aerosol outlet, and a fan support structure projecting from another side of the main body opposite the stem, the mounting flange, the stem and the fan support structure being formed integrally as a single part; a fan device for generating an air stream that passes adjacent the aerosol outlet of the stem of the discharge unit to assist in diffusing the aerosolized compound within the space to be treated; and a conduit for coupling the liquid diffusion appliance to the discharge unit.

DETAILED DESCRIPTION

Figure 1:
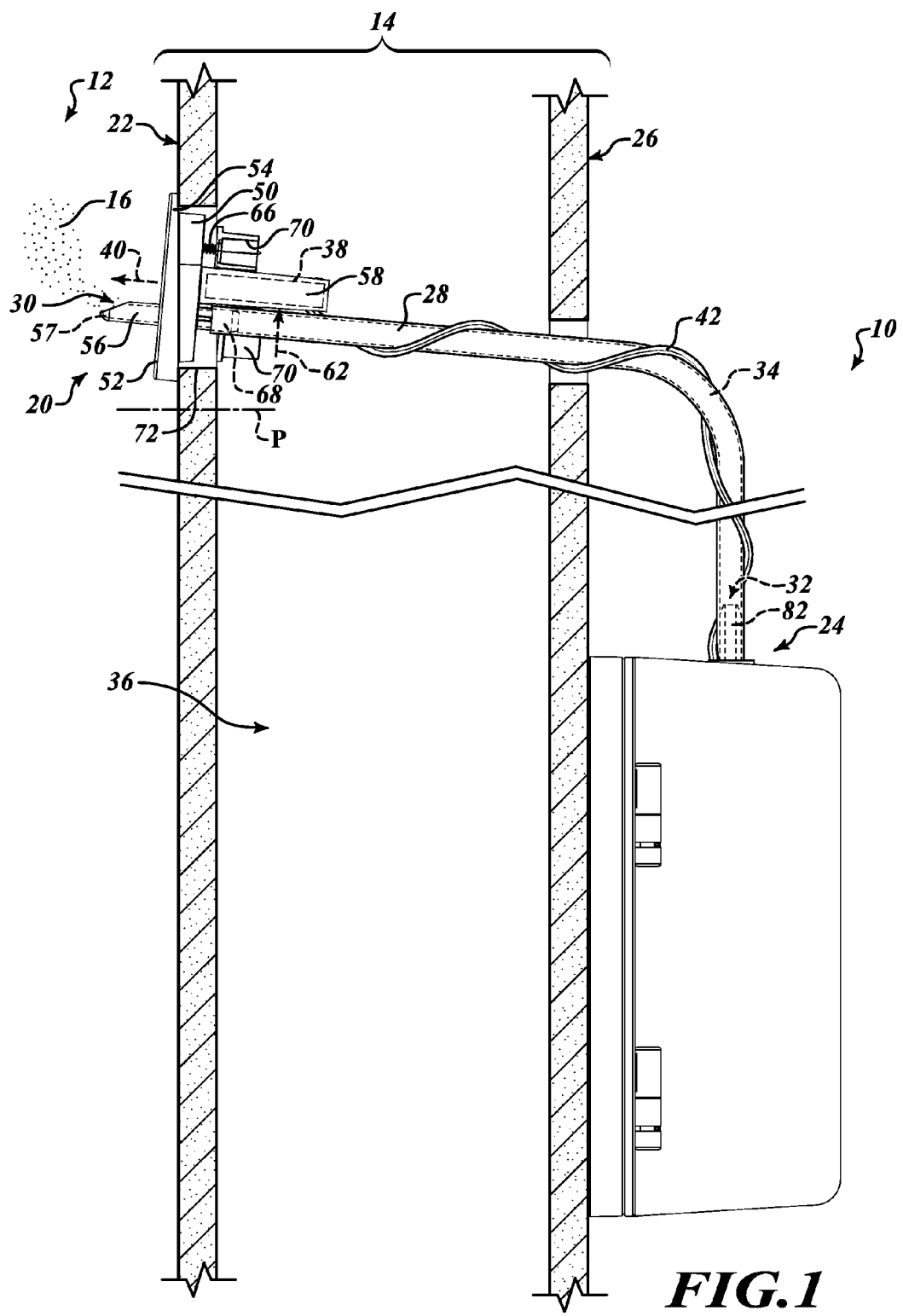
FIG. 1 is a side elevational view of an air treatment system, according to one embodiment, for treating a space at least partially enclosed by a wall with an aerosolized compound.

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with liquid diffusion appliances, components thereof and related methods of diffusing liquid may not be shown or described in detail to avoid unnecessarily obscuring descriptions of the embodiments. Examples of liquid diffusion appliances and aspects and related methods thereof which may be used in combination with the systems described herein are shown in U.S. Pat. Nos. 7,712,683, 7,930,068 and 8,855,827, all of which are incorporated herein by reference in their entirety. Further examples of liquid diffusion appliances which may be used in combination with the systems described herein include commercial and residential liquid diffusion appliances, such as the 300 and 500 series appliances (e.g., AQ550 appliance) available from the present applicant, Prolitec Inc., of Milwaukee, Wis.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The present disclosure relates generally to air treatment systems and related methods and, more specifically, to air treatment systems and related methods for treating a space at least partially enclosed by a wall with an aerosolized compound generated by a liquid diffusion appliance that is located remote from the space to be treated, including, in particular, on an opposing side of the wall.

The air treatment systems include or otherwise operate in conjunction with a liquid diffusion appliance to provide or introduce a pleasant or soothing scent (or some other type of liquid that may be used as an airborne treatment or compound) into the air space of a room or other enclosed space. The particular liquid to be dispensed by the liquid diffusion appliance may be contained within a removable cartridge within the liquid diffusion appliance. Other possible types of liquids that may be dispersed may include decontamination agents, insecticides, insect repellents, and many different types of liquids that may be desirably dispersed within an enclosed space. The present disclosure is not limited to a particular type or nature of liquid to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space, and includes spaces that are at least partially enclosed by a wall. Larger spaces, such as concert halls, casinos, lobbies, etc., may have one or more openings into the space and still have the desired characteristics to permit treatment with a diffused liquid. Other spaces may be preferably fully enclosed to permit treatment by the selected liquid. In other cases, the liquid used for treatment may preferably be used in a sealed space for maximum effectiveness or for safety reasons. Within the scope of the present disclosure, it is not intended to limit the nature, size or configuration of the space to be treated except as may be appropriate for the liquid used to treat the space and the nature of treatment desired within the space.

A source of pressurized gas (e.g., air) may be provided within or in connection with the liquid diffusion appliance that receives removable liquid cartridges. The source of pressurized gas may comprise, for example, a small air compressor or pump, an internal reservoir, or a connection to an external source of pressurized gas. Controls may be provided and configured to permit adjustment of the timing and/or pressure level of the pressurized gas or air generated by the pump or compressor that is ultimately directed into and passes through the removable cartridge. Generally, the pressurized gas is directed to atomize the liquid contained in the removable cartridge and to aid in the dispersion of an aerosolized compound into the space to be treated.

FIG. 1 shows one example embodiment of an air treatment system 10 for treating a space 12 at least partially enclosed by a wall 14 with an aerosolized compound 16. The air treatment system 10 includes a discharge unit 20 mounted to a first side 22 of the wall 14, a liquid diffusion appliance 24 mounted to a second side 26 of the wall 14 opposite the first side 22 of the wall 14, and a conduit 28 extending therebetween. The discharge unit 20 includes an aerosol outlet 30 in fluid communication with the space 12 to be treated for discharging the aerosolized compound 16 generated by the liquid diffusion appliance 24. The liquid diffusion appliance 24 includes the compound in liquid form to be aerosolized and a control system (not shown) for operating the liquid diffusion appliance 24 to generate the aerosolized compound 16 from the liquid compound and to discharge it from an appliance outlet 32. The conduit 28 couples the appliance outlet 32 of the liquid diffusion appliance 24 with the aerosol outlet 30 of the discharge unit 20 and defines a passageway 34 through the wall 14 through which the aerosolized compound 16 travels before being discharged into the space 12 to be treated.

The air treatment system 10 may further include a fan device 38 coupled to the discharge unit 20 and at least partially residing within a cavity 36 of the wall, such as a cavity defined between opposing drywall sheets. The fan device 38 may be arranged to generate an air stream that passes adjacent the aerosol outlet 30 of the discharge unit 20 to assist in diffusing the aerosolized compound 16 within the space 12 to be treated, as represented by the arrow labeled 40. The fan device 38 may be electrically coupled to the liquid diffusion appliance 24, which is mounted on the second side 26 of the wall 14, via electrical conductors 42 routed into the cavity 36 of the wall 14. In this manner, a separate power source may not be required for the fan device 38. In alternate embodiments, however, it is appreciated that the discharge unit 20 may be provided with a battery or other power source for the fan device 38. In still other embodiments, a fan device 38 may be omitted altogether.

Figure 2:
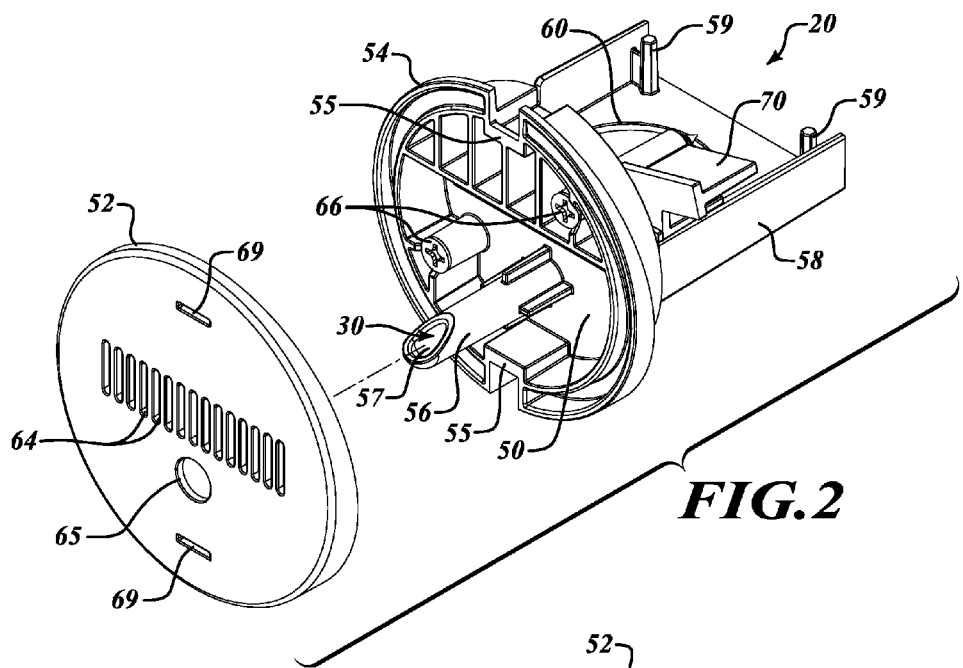
FIG. 2 is a front isometric view of a discharge unit of the air treatment system of FIG. 1, showing a cover detached from a main body portion thereof.
Figure 3:
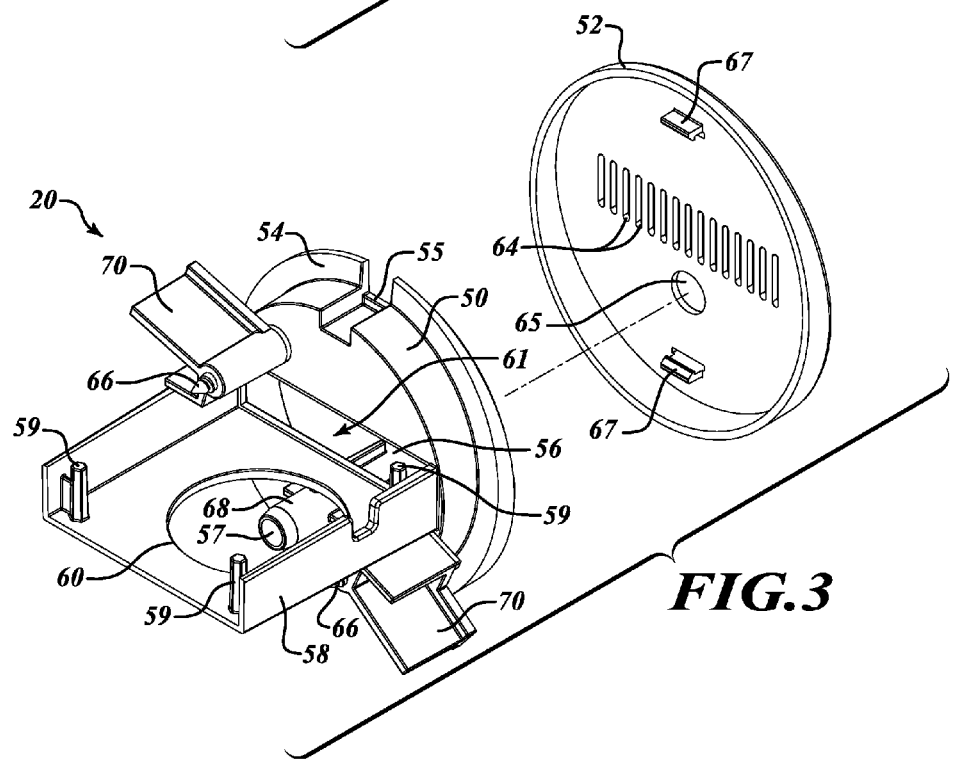
FIG. 3 is a rear isometric view of the discharge unit of the air treatment system of FIG. 1, also showing the cover detached from the main body portion thereof.

Further details of the discharge unit 20 are shown in FIGS. 2 and 3. According to the example embodiment illustrated in FIGS. 2 and 3, the discharge unit 20 includes a main body 50 and a cover plate 52 removably coupled thereto. The main body 50 includes a mounting flange 54 that abuts the wall 14, a stem 56 projecting from one side of the main body 50 and a fan support structure 58 projecting from another side of the main body 50 opposite the stem 56. The mounting flange 54, the stem 56 and the fan support structure 58 are formed integrally as a single part.

As previously described, the fan device 38 may be mounted to the fan support structure 58 and arranged to generate an air stream that passes adjacent the aerosol outlet 30, as represented by the arrow labeled 40. The fan support structure 58 may include an aperture 60 that provides access to an intake of the fan device 38, as represented by the arrow labeled 62. Advantageously, the intake of the fan device 38 may be oriented downward into the cavity 36 of the wall 14 such that falling debris or other matter in the wall cavity 36 is not drawn directly into the fan device 38. The cover plate 52 may include a grate structure 64 to enable the air stream to be discharged from the discharge unit 20 while limiting ingress of matter into the fan device 38. The grate structure 64 may align with a fan outlet aperture 61 formed in the main body 50 of the discharge unit 20 when the cover plate 52 is attached to the main body 50. The cover plate 52 may also conceal fasteners 66 used to mount the discharge unit 20 in the wall 14.

With reference to FIG. 1, the stem 56 of the discharge unit 20 includes a discharge passageway 57 that curves upwardly at a terminal end thereof to assist in directing the aerosolized compound into the air stream generated by the fan device 38. The stem 56 and the passageway 57 extending through the stem 56 are inclined relative to a horizontal reference plane P oriented perpendicular to the wall 14 such that any liquid from the aerosolized compound 16 that condenses on surfaces of the passageway 57 tends to move away from the aerosol outlet 30 toward the liquid diffusion appliance 24. In some instances, the stem 56 and the flange 54 may be configured relative to each other such that the passageway 57 extending through the stem 56 is inclined at least four or five degrees relative to the horizontal reference plane P.

With reference to FIG. 1, the main body 50 of the discharge unit 20 may further include a fitting 68 that defines a portion of the passageway 57 that extends through the discharge unit 20 and terminates at the aerosol outlet 30. The conduit 28 that extends between the liquid diffusion appliance 24 and the discharge unit 20 may be coupled to the fitting 68 to provide fluid communication between the outlet 32 of the liquid diffusion appliance 24 and the aerosol outlet 30 of the discharge unit 20.

The air treatment system 10 may further include fasteners 70 that are configured to rotate from an installation position (not shown) to a clamping position (FIGS. 2 and 3) and to be drawn from an internal cavity side of the wall 14 toward the space 12 to be treated to clamp the discharge unit 20 onto the first side 22 of the wall 14, namely onto the drywall or other structure defining the first side 22 of the wall 14.

The liquid diffusion appliance 24 may include a diffusion head (not shown) including a venturi device for generating the aerosolized compound from the liquid compound as a stream of gas moves through the venturi device to draw some of the liquid compound into the stream of gas. The aerosolized compound may then be discharged from the appliance 24 to pass through the conduit 28 and the discharge unit 20 to be discharged into the space 12 to be treated.

In view of the above, it will be appreciated that various methods of installation may be provided in connection with the air treatment systems 10 disclosed herein. According to one example embodiment, an installation method may include: mounting a discharge unit 20 to a first side 22 of a wall 14, the discharge unit 20 having an aerosol outlet 30 that is in fluid communication with a space 12 to be treated; mounting a liquid diffusion appliance 24 to a second side 26 of the wall 14 opposite the first side 22 of the wall 14, the liquid diffusion appliance 24 including a compound in liquid form to be aerosolized and including a control system for operating the liquid diffusion appliance 24 to generate an aerosolized compound 16 from the liquid compound and to discharge the aerosolized compound 16 from an appliance outlet 32 of the liquid diffusion appliance 24; and coupling the appliance outlet 32 of the liquid diffusion appliance 24 to the aerosol outlet 30 of the discharge unit 20 via a conduit 28 extending into a cavity 36 of the wall 14. The method may include positioning a fan device 38 to reside at least partially within the cavity 36 of the wall 14 and to generate an air stream that passes adjacent the aerosol outlet 30 of the discharge unit 20 to assist in diffusing the aerosolized compound 16 within the space 12 to be treated, as represented by the arrow labeled 40. The method may further include electrically coupling the fan device 38 to a circuit board or other power source provided in the liquid diffusion appliance 24 with electrical conductors 42 routed into the cavity 36 of the wall 14 for powering and controlling operation of the fan device 38. Mounting the discharge unit 20 to the first side 22 of the wall 14 may include cutting a circular hole 72 in the first side 22 of the wall 14 with a hole saw of a common size (e.g., 2⅛") and inserting the discharge unit 20 into the circular hole 72. Mounting the discharge unit to the first side 22 of the wall 14 may further include drawing fasteners 70 into contact with the wall 14 from an internal cavity side of the wall to non-destructively clamp the discharge unit 20 onto the wall 14.

Figure 4:
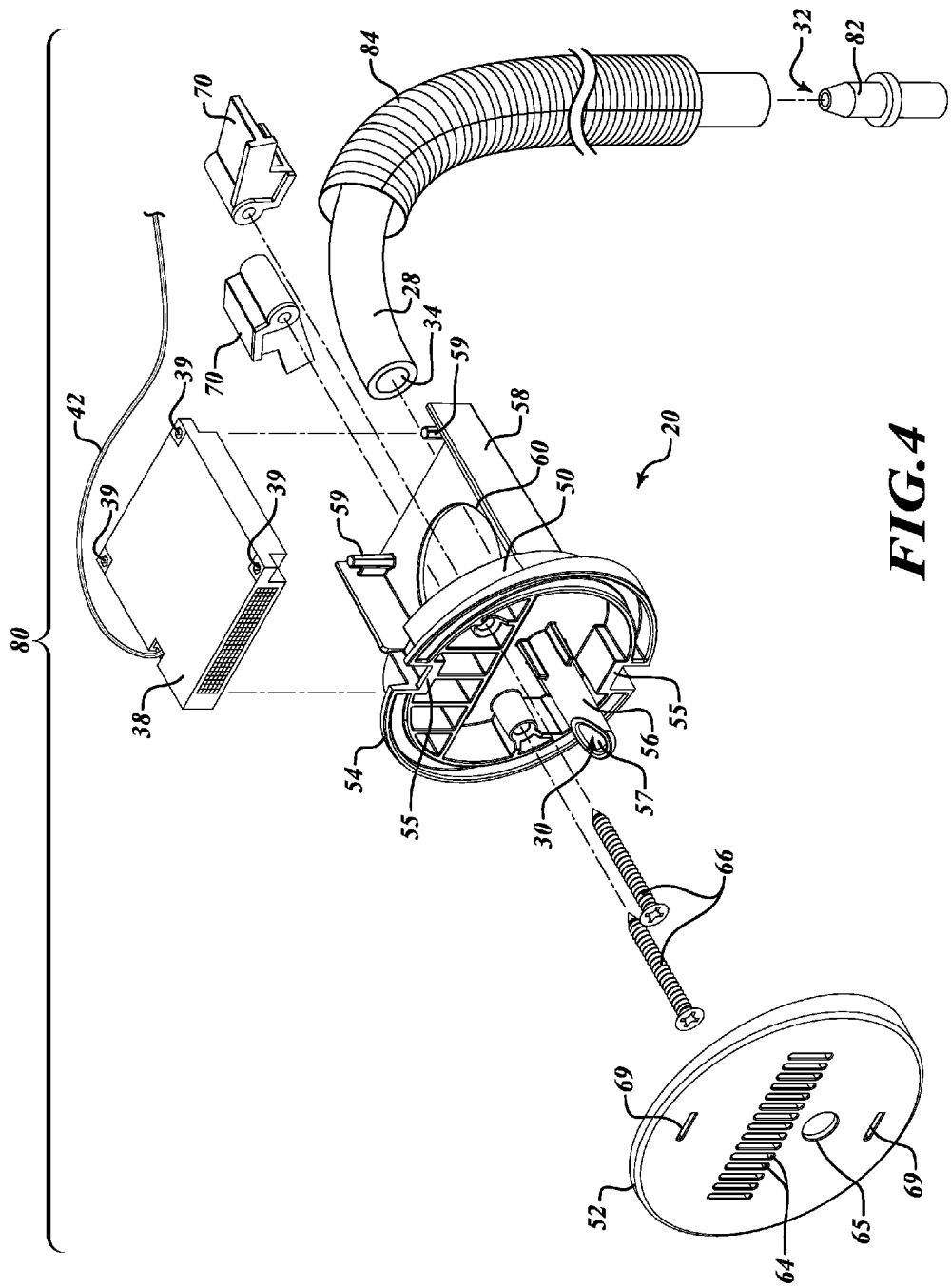
FIG. 4 is a front isometric view of a kit for a liquid diffusion appliance for forming the air treatment system of FIG. 1.

With reference to FIG. 4, a kit 80 may be provided for positioning a liquid diffusion appliance 24 remote from a space 12 to be treated by the appliance 24. The kit 80 may include: a wall mountable discharge unit 20 comprising a main body 50, the main body including a mounting flange 54, a stem 56 projecting from one side of the main body 50, which includes an aerosol outlet 30, and a fan support structure 58 projecting from another side of the main body 50 opposite the stem 56, the mounting flange 54, the stem 56 and the fan support structure 58 being formed integrally as a single part; a fan device 38 for generating an air stream that passes adjacent the aerosol outlet 30 of the stem 56 of the discharge unit 20 to assist in diffusing the aerosolized compound 16 within the space 12 to be treated; and a conduit 28 for coupling the liquid diffusion appliance 24 to the discharge unit 20. The kit 80 may further include an adapter 82 for securing the conduit 28 to the liquid diffusion appliance 24, which may subsequently define or otherwise be in fluid communication with the appliance outlet 32 of the liquid diffusion appliance 24. The fan device 38 may be provided with electrical conductors 42 (e.g., insulated wires or an electrical cable) for supplying power to the fan device 38 from a power source associated with the liquid diffusion appliance 24. A sheath, sleeve, split tubing 84, or other protector may be provided to cover at least a portion of the length of the conduit 28 extending into the wall 14. The electrical conductors 42 for the fan device 38 may be routed with the conduit 28 and at least partially surrounded by the sheath, sleeve, split tubing 84, or other protector. The kit 80 may further include suitable fasteners 66, 70 for securing the discharge unit 20 to the first side 22 of the wall 14.

With reference to FIG. 4, the fan support structure 58 may include a plurality of upstanding columnar projections 59 that are sized and spaced to be inserted into a corresponding plurality of apertures 39 provided in the fan device 38. Each columnar projection 59 may comprise a polygonal shaped cross-section and may taper with increasing distance away from the fan support structure 58. The apertures 39 in the fan device 38 may have a cylindrical profile that interfaces with each respective columnar projection 59 at a plurality of discrete areas of contact to securely attach the fan device 38 to the fan support structure 58 without separate fasteners.

With reference to FIGS. 2 and 3, the cover plate 52 may include a plurality of coupling devices 67 (e.g., resilient clips) formed integrally therewith for engaging corresponding coupling devices 55 (e.g., catches) of the main body 50 for removably securing the cover plate 52 to the main body 50. The cover plate 52 may be detached from the main body 50 by accessing the coupling devices 67 via corresponding access apertures 69 in the cover plate 52. A nozzle aperture 65 may be provided in the cover plate 52 for enabling the stem 56 to pass through and project from the cover plate 52. Thus, in the assembled configuration, as shown in FIG. 1, only the stem 56 and the cover plate 52 may be readily seen by an occupant of the space 12 to be treated. Accordingly, the system 10 may be particularly inconspicuous to occupants of the space 12. In addition, the liquid diffusion appliance 24 may be readily accessible on the other side of the wall 14 for servicing and the like.

It is also appreciated that aspects and features of the various embodiments described above may be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application No. 62/220,155, filed Sep. 17, 2015, are incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A system for treating a space at least partially enclosed by a wall with an aerosolized compound, the system comprising:
   a discharge unit mounted to a first side of the wall, the discharge unit comprising a main body and a cover plate removably coupled thereto, the main body including a mounting flange that abuts the wall, a stem projecting from one side of the main body which includes an aerosol outlet in fluid communication with the space to be treated, and a fan support structure projecting from another side of the main body opposite the stem, and wherein the mounting flange, the stem and the fan support structure are formed integrally as a single part;
   a liquid diffusion appliance mounted to a second side of the wall opposite the first side of the wall, the liquid diffusion appliance including the compound in liquid form to be aerosolized and including a control system for operating the liquid diffusion appliance to generate the aerosolized compound from the liquid compound and to discharge the aerosolized compound from an appliance outlet of the liquid diffusion appliance; and
   a conduit coupling the appliance outlet of the liquid diffusion appliance with the aerosol outlet of the discharge unit, the conduit defining a passageway through the wall through which the aerosolized compound travels to be discharged into the space to be treated.

2. The system of claim 1, further comprising:
   a fan device coupled to the discharge unit and at least partially residing within a cavity of the wall, the fan device arranged to generate an air stream that passes adjacent the aerosol outlet of the discharge unit to assist in diffusing the aerosolized compound within the space to be treated.

3. The system of claim 2 wherein the fan device is electrically coupled to the liquid diffusion appliance mounted on the second side of the wall via electrical conductors routed into the cavity of the wall.

4. The system of claim 2 wherein the stem of the discharge unit includes a discharge passageway that curves upwardly at a terminal end thereof to assist in directing the aerosolized compound into the air stream generated by the fan device.

5. The system of claim 2 wherein the fan device includes an intake oriented downward into the cavity of the wall.

6. The system of claim 2 wherein the cover plate of the discharge unit includes a grate structure to limit ingress of matter into the fan.

7. The system of claim 1 wherein the discharge unit includes a passageway extending through the stem, the stem and passageway extending therethrough being inclined relative to a horizontal reference plane oriented perpendicular to the wall such that any liquid from the aerosolized compound that condenses on surfaces of the passageway tends to move away from the aerosol outlet toward the liquid diffusion appliance.

8. The system of claim 1 wherein the main body further includes an aperture through which the air stream generated by the fan passes, and wherein the cover plate includes a grate structure aligned with the aperture in the main body.

9. The system of claim 1 wherein the main body of the discharge unit further includes a fitting that defines a portion of a passageway that extends through the discharge unit and terminates at the aerosol outlet, and wherein the conduit that extends between the liquid diffusion appliance and the discharge unit is coupled to the fitting.

10. The system of claim 1 wherein the discharge unit is mounted to the wall with fasteners and the cover plate conceals the fasteners from view from the first side of the wall.

11. The system of claim 1 wherein the liquid diffusion appliance includes a diffusion head including a venturi device for generating the aerosolized compound from the liquid compound as a stream of gas moves through the venturi device to draw in some of the liquid compound into the stream of gas.

12. A system for treating a space at least partially enclosed by a wall with an aerosolized compound, the system comprising:
   a discharge unit mounted to a first side of the wall, the discharge unit comprising a main body including a mounting flange and a stem projecting from one side of the main body which includes an aerosol outlet in fluid communication with the space to be treated, the mounting flange and the stem being formed integrally as a single part and being configured relative to each other such that a passageway extending through the stem is inclined at least five degrees relative to a horizontal reference plane that is oriented perpendicular to the wall while the mounting flange abuts the wall;
   a liquid diffusion appliance mounted to a second side of the wall opposite the first side of the wall, the liquid diffusion appliance including the compound in liquid form to be aerosolized and including a control system for operating the liquid diffusion appliance to generate the aerosolized compound from the liquid compound and to discharge the aerosolized compound from an appliance outlet of the liquid diffusion appliance; and
   a conduit coupling the appliance outlet of the liquid diffusion appliance with the aerosol outlet of the discharge unit, the conduit defining a passageway through the wall through which the aerosolized compound travels to be discharged into the space to be treated.

13. The system of claim 12 wherein the main body of the discharge unit further comprises a fan support structure projecting from another side of the main body opposite the stem, and wherein the mounting flange, the stem and the fan support structure are formed integrally as a single part.

14. A system for treating a space at least partially enclosed by a wall with an aerosolized compound, the system comprising:
   a discharge unit mounted to a first side of the wall, the discharge unit having an aerosol outlet in fluid communication with the space to be treated;
   a liquid diffusion appliance mounted to a second side of the wall opposite the first side of the wall, the liquid diffusion appliance including the compound in liquid form to be aerosolized and including a control system for operating the liquid diffusion appliance to generate the aerosolized compound from the liquid compound and to discharge the aerosolized compound from an appliance outlet of the liquid diffusion appliance;

a conduit coupling the appliance outlet of the liquid diffusion appliance with the aerosol outlet of the discharge unit, the conduit defining a passageway through the wall through which the aerosolized compound travels to be discharged into the space to be treated; and fasteners configured to rotate from an installation position to a clamping position and to be drawn from an internal cavity side of the wall toward the space to be treated to clamp the discharge unit onto the first side of the wall.

\* \* \* \* \*